(12) United States Patent
Ishii et al.

(10) Patent No.: US 7,074,970 B2
(45) Date of Patent: Jul. 11, 2006

(54) PROCESS FOR PRODUCING VINYL ETHER COMPOUNDS

(75) Inventors: Yasutaka Ishii, Takatsuki (JP); Tatsuya Nakano, Himeji (JP); Keizo Inoue, Himeji (JP)

(73) Assignee: Daicel Chemical Industries, Ltd., Sakai (JP)

( * ) Notice: Subject to any disclaimer, the term of this patent is extended or adjusted under 35 U.S.C. 154(b) by 0 days.

(21) Appl. No.: 10/231,115

(22) Filed: Aug. 30, 2002

(65) Prior Publication Data

US 2003/0083529 A1    May 1, 2003

(30) Foreign Application Priority Data

Aug. 30, 2001 (JP) .............................. 2001-261632

(51) Int. Cl.
    *C07C 43/00* (2006.01)
(52) U.S. Cl. ...................................... 568/688; 568/687
(58) Field of Classification Search ............... 568/687, 568/688, 689, 690
    See application file for complete search history.

(56) References Cited

U.S. PATENT DOCUMENTS 2,579,411 A * 12/1951 Adelman ................. 560/183
2,969,395 A *  1/1961 Nedwick et al. ......... 564/391
3,936,473 A *  2/1976 Symon et al. ............ 549/290

FOREIGN PATENT DOCUMENTS

| EP | 1 246 013 A2 | 10/2002 |
| FR | 2 213 928 | 8/1974 |
| JP | 2001-220364 | * 8/2001 |

OTHER PUBLICATIONS

Okimoto et al., Development of a Highly Efficient Catalytic Method for Synthesis of Vinyl Ethers J. Am. Chem. Soc. 124(8) 2002.*
McKeon et al., The palladium (II) catalyzed vinyl interchange reaction-II, Tetrahedron (1972), 28(2), 233-8.*
Journal of the American Chemical Society (1953), 75, 2678-82, CAPLUS online citation attached [retrieved on Feb. 17, 2006] Chemical Abstracts, Columbus OH, USA.*
D. M. Jones et al., J. Chem. Soc., 1965, pp. 1560-1561 (Database Accession No. 6712483).
Mikhant'ev et al., J. Org. Chem. USSR, vol. 7, 1971, pp. 119 (Database Accession No. 2995060).

I. E. Marko et al., Tetrahedron Lett., vol. 35, No. 17, 1994, pp. 2771-2774 (Database Accession No. 6799833).
E. Cabianca et al., Syn. Lett., vol. 12, 2001, pp. 1962-1964 (Database Accession No. 8904968).
Y. Okimoto et al., J. Am Chem. Soc., vol. 124, No. 8, 2002, pp. 1590-1591 (Database Accession No. 9053450).
Fringuelli et al., J. Org. Chem., 2001, 66, 4661-4666.
Bailey et al., J. Org. Chem, 1991, 56, 846-849.
Reppe, Justus Liebigs Annalen Der Chemie, Verlag Chemie, DE, vol. 601, 1956, pp. 81-138 (with partial English translation (p. 104-105)).

(Continued)

Primary Examiner—Johann Richter
Assistant Examiner—Karl Puttlitz
(74) Attorney, Agent, or Firm—Birch, Stewart, Kolasch & Birch, LLP

(57) ABSTRACT

A process produces vinyl ether compounds and includes allowing a vinyl ester compound represented by following Formula (1):

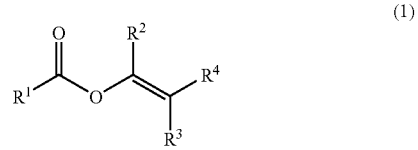

(1)

wherein $R^1$, $R^2$, $R^3$ and $R^4$ are the same or different and are each a hydrogen atom or an organic group, to react with a hydroxy compound represented by following Formula (2):

$$R^5OH \qquad (2)$$

wherein $R^5$ is an organic group, in the presence of at least one transition element compound to thereby yield a vinyl ether compound represented by following Formula (3):

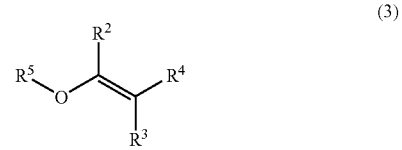

(3)

wherein $R^2$, $R^3$, $R^4$ and $R^5$ have the same meanings as defined above. Such transition element compounds include iridium compounds and other compounds containing Group VIII elements.

6 Claims, No Drawings

OTHER PUBLICATIONS

Villar et al., Organic Letters, vol. 2, No. 8, 2000, pp. 1061-1064.

H. G. Posner et al., Tetrahedron Letters, vol. 27, No. 6, 1986, pp. 667-670 (Database Accession No. 2553996).

W. F. Bailey et al., Tetrahedron Letters, vol. 32, No. 35, 1991, pp. 4425-4426 (Database Accession No. 4798545).

R. E. Keller et al., J. Gen. Chem. USSR, vol. 31, 1961, pp. 3004-3005 (Database Accession No. 7267192).

B. F. Kukharev et al., Russ. J. Org. Chem., vol. 31, No. 5, 1995, pp. 595-596 (Database Accession No. 7578694).

C. Pascual et al., Helv. Chim. Acta, vol. 49, 1966, pp. 164-168 (Database Accession No. 2523395).

Brugel et al., Chemical Abstracts, vol. 54, No. 6, 1960, Abstract No. 5246 (Database Accession No. 2356300).

M. F. Shostakovskii et al., Bull. Acad. Sci. USSR Div. Chem. Sci. 1961, pp. 105-111 (Database Accession No. 2517051).

* cited by examiner

PROCESS FOR PRODUCING VINYL ETHER COMPOUNDS

BACKGROUND OF THE INVENTION

1. Field of the Invention

The present invention relates to vinyl ether compounds that are useful as raw materials for pharmaceutical drugs, agricultural chemicals, and polymers, as well as to processes for producing such vinyl ether compounds.

2. Description of the Related Art

Vinyl ether compounds are useful as raw materials for pharmaceutical drugs, agricultural chemicals, and other fine chemicals and as raw materials for polymers such as resist resins, optical plastics, transparent resins, and crosslinking resins. Among them, vinyl ether compounds each having an alicyclic skeleton, a lactone skeleton, or another non-aromatic cyclic skeleton are promising material monomers for resist resins, since they can improve transparency and resistance to dry etching when they are used as comonomers of such polymers. Vinyl ether compounds each having plural vinyl groups are suitable as material monomers for crosslinking resins, since they can impart high solvent resistance to the resulting polymers. In addition, such vinyl ether compounds develop odor and irritate the skin less than acrylic compounds and are excellent in handleability and workability. However, there are less types of vinyl ether compounds at higher cost than acrylic compounds (monomers) on the market, which do not sufficiently fill the needs for such vinyl ether compounds.

The vinyl ether compounds have been prepared, for example, by a process in which acetylene is allowed to react with an alcohol by catalysis of an alkali metal hydroxide or an alkali metal alcoholate. However, this process is disadvantageous in that it uses acetylene that is difficult to handle. Alternatively, U.S. Pat. No. 2,579,411 discloses a process for producing a vinyl ether compound, in which an alcohol is allowed to react with a vinyl ester in the presence of a mercury salt of a strong acid at a temperature of from −75° C. to −15° C. However, this process requires the use of highly toxic mercury, needs a reaction at very low temperatures, and is not suitable as a process for commercial production.

SUMMARY OF THE INVENTION

Accordingly, an object of the present invention is to provide a process for easily producing a vinyl ether compound under mild conditions.

Another object of the present invention is to provide a versatile process for producing vinyl ether compounds.

Yet another object of the present invention is to provide a novel vinyl ether compound.

After intensive investigations to achieve the above objects, the present inventors have found that a corresponding vinyl ether compound can easily be obtained under mild conditions by allowing a vinyl ester compound to react with a hydroxy compound in the presence of a specific catalyst. They also have succeeded to produce novel vinyl ether compounds. The present invention has been accomplished based on these findings.

Specifically, the present invention provides, in an aspect, a process for producing vinyl ether compounds. The process includes the step of allowing a vinyl ester compound represented by following Formula (1):

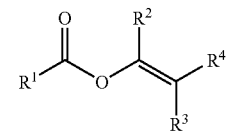

(1)

wherein $R^1$, $R^2$, $R^3$ and $R^4$ are the same or different and are each a hydrogen atom or an organic group, to react with a hydroxy compound represented by following Formula (2):

$$R^5OH \qquad (2)$$

wherein $R^5$ is an organic group, in the presence of at least one transition element compound to thereby yield a vinyl ether compound represented by following Formula (3):

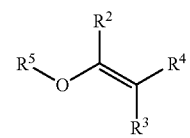

(3)

wherein $R^1$, $R^3$, $R^4$ and $R^5$ have the same meanings as defined above.

Such transition element compounds include, for example, iridium compounds and other compounds comprising Group VIII elements of the Periodic Table of Elements. In the process, the vinyl ester compound represented by Formula (1) may be allowed to react with the hydroxy compound represented by Formula (2) in the presence of a base.

In another aspect, the present invention provides a vinyl ether compound represented by following Formula (4):

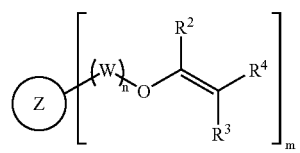

(4)

wherein ring Z is any one of cyclic groups represented by following Formulae (5) through (12):

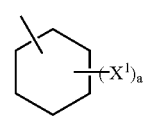

(5)

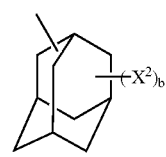

(6)

-continued

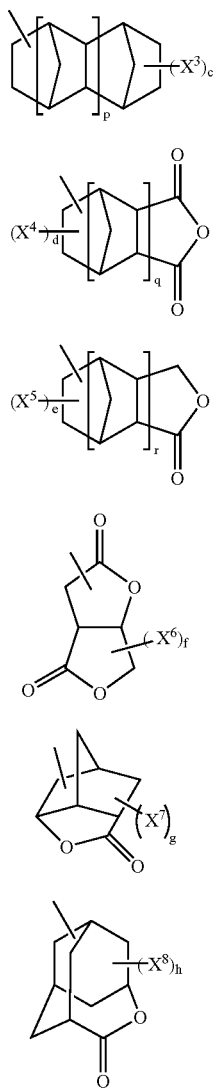

wherein $X^1$, $X^2$, $X^3$, $X^4$, $X^5$, $X^6$, $X^7$, and $X^8$ are each a substituent combined with an atom constituting each ring and are each a halogen atom, an alkyl group, a haloalkyl group, an aryl group, a hydroxyl group which may be protected by a protecting group, a hydroxymethyl group which may be protected by a protecting group, an amino group which may be protected by a protecting group, a carboxyl group which may be protected by a protecting group, a sulfo group which may be protected by a protecting group, an oxo group, a nitro group, a cyano group, or an acyl group which may be protected by a protecting group, wherein, when there are two or more substituents $X^1$s, these $X^1$s may be combined to form a ring containing four or more members with a carbon atom constituting the cyclohexane ring in Formula (5);

a, b, c, d, e, f, g, and h are each an integer of 0 or more, wherein, when a, b, c, d, e, f, g or h is 2 or more, the substituents in the parentheses may be the same or different; and p, q, and r are each an integer of from 0 to 3;

W is a divalent hydrocarbon group;

$R^2$, $R^3$, and $R^4$ are the same or different and are each a hydrogen atom or an organic group;

n is 0 or 1; and m is an integer of from 1 to 8, wherein groups in the parentheses may be the same or different when m is 2 or more;

wherein a in Formula (5) is 1 or more and b in Formula (6) is 1 or more when n is 0 and m is 1; and wherein c is 1 or more when p is 0 or 1, and $X^3$ is a group other than hydroxyl group when p is 0 and c is 1 in Formula (7).

The process of the present invention can easily produce vinyl ether compounds under mild conditions. In addition, it is versatile and can efficiently produce a broad range of vinyl ether compounds.

The present invention also provides novel vinyl ether compounds.

The "vinyl ether compounds" and "vinyl ester compounds" as used herein also include compounds in which a hydrogen atom of a vinyl group is substituted with a substituent. The "transition elements" include Group IIIA elements, Group IVA elements, Group VA elements, Group VIA elements, Group VIIA elements, Group VIII elements, and Group IB elements of the Periodic Table of Elements. The term "organic group" as used herein is used in a wide meaning and includes not only carbon-atom-containing groups but also halogen atoms, nitro group, sulfonic acid group, and other groups containing non-metallic atoms.

DESCRIPTION OF THE PREFERRED EMBODIMENTS

Transition Element Compounds

According to the present invention, transition element compounds (inclusive of elementary substances of transition elements) are used as a catalyst. Each of these transition element compounds can be used alone or in combination. Such transition elements include lanthanum, cerium, and other Group IIIA elements (in particular, lanthanoid elements); titanium, zirconium, and other Group IVA elements; vanadium and other Group VA elements; chromium, molybdenum, tungsten, and other Group VIA elements; manganese and other Group VIIA elements; iron, cobalt, nickel, ruthenium, rhodium, palladium, osmium, iridium, platinum, and other Group VIII elements; and copper, silver, and other Group IB elements. Among them, Group VIII elements are preferred, of which platinum group elements including ruthenium, rhodium, palladium, osmium, iridium, and platinum are typically preferred. In particular, iridium is specifically preferred.

Transition element compounds include, but are not limited to, elementary substances (metals), oxides, sulfides, hydroxides, halides (fluorides, chlorides, bromides, and iodides), and sulfates of transition elements, oxoacids or salts thereof, and inorganic complexes containing transition elements, and other inorganic compounds; cyanides, salts of organic acids (e.g., acetates), organic complexes, and other organic compounds of transition elements. Among them, organic complexes are typically preferred. Ligands constituting such complexes include known ligands. The transition elements in the transition element compounds each have a valency of from about 0 to about 6, and preferably from about 0 to about 3. In particular, iridium in the iridium compounds preferably has a valency of 1 or 3.

Examples of the transition element compounds include, by taking iridium compounds as an example, metal iridium, iridium oxide, iridium sulfide, iridium hydroxide, iridium fluoride, iridium chloride, iridium bromide, iridium iodide, iridium sulfate, iridic acid and salts thereof (e.g., potassium iridate), inorganic iridium complexes [e.g., hexaammineiridlum(III) salts, and chloropentaammineiridium(III) salts], and other inorganic compounds; iridium cyanide, organic iridium complexes, and other organic compounds. Such organic complexes include, but are not limited to, tris (acetylacetonato)iridium, dodecacarbonyltetrairidium(0), chlorotricarbonyliridium(I), di-μ-chlorotetrakis(cyclooctene)diiridium(I), di-μ-chlorotetrakis(ethylene)diiridium(I), di-μ-chlorobis(1,5-cyclooctadiene)diiridium(I), di-μ-chlorodichlorobis(pentamethylcyclopentadienyl)diiridium(III), trichlorotris(triethylphosphine)iridium(III), pentahydridobis(trimethylphosphine)iridium(V), chlorocarbonylbis(triphenylphosphine)iridium(I), chloroethylenebis (triphenylphosphine)iridium(I), (pentamethylcyclopentadienyl)dicarbonyliridium(I), bis{1, 2-bis(diphenylphosphino)ethane}iridium(I) chloride, pentamethylcyclopentadienylbis(ethylene)iridium(I), carbonylmethylbis(triphenylphosphine)iridium(I), (1,5-cylooctadiene)(diphosphine)iridium(I) halides, 1,5-cyclooctadiene(1,2-bis(diphenylphosphino)ethane)iridium (I) haxafluorophosphate, (1,5-cyclooctadiene)bis (trialkylphosphine)iridium(I) halides, bis(1,5-cyclooctadiene)iridium tetrafluoroborate, and (1,5-cyclooctadiene)(acetonitrile)iridium tetrafluoroborate.

Preferred iridium compounds include iridium complexes, of which organic iridium complexes are typically preferred. Among them, organic iridium complexes each having a specific ligand are especially preferred. Such specific ligands include, for example, cyclopentene, dicyclopentadiene, cyclooctene, 1,5-cyclooctadiene, ethylene, pentamethylcyclopentadiene, benzene, toluene, and other unsaturated hydrocarbons; acetonitrile and other nitrites; and tetrahydrofuran and other ethers. Examples of such preferred organic iridium complexes are di-μ-chlorotetrakis(cyclooctene)diiridium(I), di-μ-chlorotetrakis(ethylene)diiridium(I), di-μ-chlorobis(1,5-cyclooctadiene)diiridium(I), bis (1,5-cyclooctadiene)iridium tetrafluoroborate, and (1,5-cyclooctadiene)(acetonitrile)iridium tetrafluoroborate. Each of these iridium compounds can be used alone or in combination with each other and can be used in combination with the other transition element compounds.

The other transition element compounds than the iridium compounds include compounds corresponding to the iridium compounds, such as dichloro(1,5-cyclooctadiene)ruthenium, dichloro(1,5-cyclooctadiene)platinum, and dichlorobis(1,5-cyclooctadiene)dirhodium. Among the other transition element compounds than the iridium compounds, preferred are organic complexes each containing a specific ligand such as cyclopentene, dicyclopentadiene, cyclooctene, 1,5-cyclooctadiene, ethylene, pentamethylcyclopentadiene, benzene, toluene, and other unsaturated hydrocarbons; acetonitrile and other nitrites; and tetrahydrofuran and other ethers.

The transition element compound can be used as intact or being supported by a carrier (support). Such carriers include conventional carriers for supporting catalysts, such as silica, alumina, silica-alumina, zeolite, titania, magnesia, and other metal oxides, as well as activated carbon. In a catalyst supported by a carrier, the amount of the transition element compound is, for example, from about 0.1% to 50% by weight, and preferably from about 1% to about 20% by weight relative to the weight of the carrier. The catalyst transition element compound can be supported by the carrier according to a conventional procedure such as impregnation, precipitation, and ion exchange.

The amount of the transition element compound is, for example, from about 0.0001 to about 1 mole, preferably from about 0.001 to about 0.3 mole, and more preferably from about 0.005 to about 0.1 mole per mole of the hydroxy compound used as a reaction component.

Vinyl Ester Compounds

In the vinyl ester compounds represented by Formula (1) the substituents $R^1$, $R^2$, $R^3$, and $R^4$ are each a hydrogen atom or an organic group. The organic group herein may be any organic group that does not adversely affect the reaction, such as an organic group that is not reactive under reaction conditions in the process of the present invention. Such organic groups include, but are not limited to, halogen atoms such as fluorine, chlorine, bromine and iodine atoms, hydrocarbon groups, heterocyclic groups, substituted oxycarbonyl groups (e.g., alkoxycarbonyl groups, aryloxycarbonyl groups, aralkyloxycarbonyl groups, and cycloalkyloxycarbonyl groups), carboxyl group, substituted or unsubstituted carbamoyl groups, cyano group, nitro group, sulfur acid groups, sulfur acid ester groups, acyl groups (e.g., acetyl group and other aliphatic acyl groups; and benzoyl group and other aromatic acyl groups), alkoxy groups (e.g., methoxy, ethoxy, and other $C_1$–$C_6$ alkoxy groups), and N,N-disubstituted amino groups (e.g., N,N-dimethylamino group, and piperidino group), and groups each comprising two or more of these groups combined with each other. The carboxyl group and other groups may be protected by protecting groups which are known or conventionally used in the field of organic synthesis. Among these organic groups, hydrocarbon groups and heterocyclic groups are preferred.

The hydrocarbon groups and heterocyclic groups also include hydrocarbon groups and heterocyclic groups each having at least one substituent. The hydrocarbon groups include aliphatic hydrocarbon groups, alicyclic hydrocarbon groups, aromatic hydrocarbon groups, and groups comprising these groups combined with each other. The aliphatic hydrocarbon groups include, but are not limited to, methyl, ethyl, propyl, isopropyl, butyl, isobutyl, s-butyl, t-butyl, pentyl, hexyl, decyl, dodecyl, and other alkyl groups each containing from about 1 to about 20, preferably from about 1 to about 10, and more preferably from about 1 to about 3 carbon atoms; vinyl, allyl, 1-butenyl, and other alkenyl groups each containing from about 2 to about 20, preferably from about 2 to about 10, and more preferably 2 or 3 carbon atoms; ethynyl, propynyl, and other alkynyl groups each containing from about 2 to about 20, preferably from about 2 to about 10, and more preferably 2 or 3 carbon atoms.

The alicyclic hydrocarbon groups include, but are not limited to, cyclopropyl, cyclobutyl, cyclopentyl, cyclohexyl, cyclooctyl, and other cycloalkyl groups each containing from about 3 to about 20, preferably from about 3 to 15, and more preferably from about 5 to about 8 members; cyclopentenyl, cyclohexenyl, and other cycloalkenyl groups each containing from about 3 to about 20, preferably from about 3 to about 15, and more preferably from about 5 to about 8 members; perhydronaphthalen-1-yl group, norbornyl, adamantyl, tetracyclo[$4.4.0.1^{2,5}.1^{7,10}$]dodec-3-yl group, and other bridged hydrocarbon groups. The aromatic hydrocarbon groups include, but are not limited to, phenyl, naphthyl, and other aromatic hydrocarbon groups each containing form about 6 to about 14, and preferably from about 6 to about 10 carbon atoms.

Hydrocarbon groups each comprising an aliphatic hydrocarbon group and an alicyclic hydrocarbon group combined with each other include, for example, cyclopentylmethyl, cyclohexylmethyl, 2-cyclohexylethyl, and other cycloalkyl-alkyl groups (e.g., $C_3$–$C_{20}$ cycloalkyl-$C_1$–$C_4$ alkyl groups). Hydrocarbon groups each comprising an aliphatic hydrocarbon group and an aromatic hydrocarbon group combined with each other include, for example, aralkyl groups such as $C_7$–$C_{18}$ aralkyl groups; and alkyl-substituted aryl groups such as phenyl or naphthyl group on which about one to about four $C_1$–$C_4$ alkyl groups are substituted.

Preferred hydrocarbon groups include $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{15}$ cycloalkyl-$C_1$–$C_4$ alkyl groups, and $C_7$–$C_{14}$ aralkyl groups.

The hydrocarbon groups may each have at least one substituent. Such substituents include, but are not limited to, halogen atoms, oxo group, hydroxyl group, substituted oxy groups (e.g., alkoxy groups, aryloxy groups, aralkyloxy groups, and acyloxy groups), carboxyl group, substituted oxycarbonyl groups (e.g., alkoxycarbonyl groups, aryloxycarbonyl groups, and aralkyloxycarbonyl groups), substituted or unsubstituted carbamoyl groups, cyano group, nitro group, substituted or unsubstituted amino groups, sulfo group, and heterocyclic groups. The hydroxyl group and carboxyl group just mentioned above may be protected by a protecting group conventionally used in the field of organic synthesis. The alicyclic hydrocarbon groups and aromatic hydrocarbon groups may have aromatic or non-aromatic heterocyclic rings fused to their rings.

Heterocyclic rings constituting the heterocyclic groups in $R^1$ and the other substituents include aromatic heterocyclic rings and non-aromatic heterocyclic rings. Such heterocyclic rings include, but are not limited to, heterocyclic rings each containing at least one oxygen atom as a hetero atom (e.g., furan, tetrahydrofuran, oxazole, isoxazole, γ-butyrolactone, and other 5-membered rings; 4-oxo-4H-pyran, tetrahydropyran, morpholine, and other 6-membered rings; benzofuran, isobenzofuran, 4-oxo-4H-chromene, chroman, isochroman, and other fused rings; 3-oxatricyclo[4.3.1.1$^{4,8}$] undecan-2-one ring, 3-oxatricyclo[4.2.1.0$^{4,8}$]nonan-2-one ring, and other bridged rings); heterocyclic rings each containing at least one sulfur atom as a hetero atom (e.g., thiophene, thiazole, isothiazole, thiadiazole, and other 5-membered rings; 4-oxo-4H-thiopyran, and other 6-membered rings; benzothiophene ring and other fused rings); heterocyclic rings each containing at least one nitrogen atom as a hetero atom (e.g., pyrrole, pyrrolidine, pyrazole, imidazole, triazole, and other 5-membered rings; pyridine, pyridazine, pyrimidine, pyrazine, piperidine, piperazine, and other 6-membered rings; indole, indoline, quinoline, acridine, naphthyridine, quinazoline, purine, and other fused rings). The heterocyclic groups may each have at least one substituent. Such substituents include, for example, alkyl groups (e.g., methyl, ethyl, and other $C_1$–$C_4$ alkyl groups), cycloalkyl groups, aryl groups (e.g., phenyl and naphthyl groups), as well as the substituents which the hydrocarbon groups may have.

Preferred substituents $R^1$, $R^2$, $R^3$ and $R^4$ include hydrogen atoms and hydrocarbon groups such as $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Among them, methyl group and other $C_1$–$C_3$ alkyl groups and phenyl group are typically preferred as $R^1$, and hydrogen atom, methyl group and other $C_1$–$C_3$ alkyl groups are typically preferred as $R^2$, $R^3$, and $R^4R$.

Typical examples of the vinyl ester compounds represented by Formula (1) include vinyl acetate, isopropenyl acetate, 1-propenyl acetate, 2-methyl-1-propenyl acetate, 1,2-dimethyl-1-propenyl acetate, vinyl formate, vinyl propionate, and vinyl benzoate.

Hydroxy Compounds

According to the process of the present invention, a broad range of hydroxy compounds such as alcohols and phenols can be used as a reaction component. In Formula (2), the organic group in $R^5$ can be any of organic groups as long as they do not adversely affect the reaction, such as organic groups that are not reactive under reaction conditions in the process of the present invention. Such organic groups include, for example, organic groups similar to those exemplified in the substituents $R^1$, $R^2$, $R^3$ and $R^4$. Typical examples of the organic groups are hydrocarbon groups and heterocyclic groups. Such hydrocarbon groups and heterocyclic groups include those exemplified in the substituents $R^1$, $R^2$, $R^3$ and $R^4$. The hydrocarbon groups and heterocyclic groups also include hydrocarbon groups and heterocyclic groups each having at least one substituent, as well as those each having a ring fused thereto. Such substituents are not specifically limited, as long as they do not adversely affect the reaction, and include the substituents which the hydrocarbon groups and heterocyclic groups in $R^1$, $R^2$, $R^3$ and $R^4$ may have.

The hydroxy compounds include, for example, primary alcohols, secondary alcohols, tertiary alcohols, and phenols. The hydroxy compounds may each have plural hydroxyl groups and may be whichever of monohydric alcohols, dihydric alcohols, polyhydric alcohols, monohydric phenols, dihydric phenols, and polyhydric-phenols.

Typical primary alcohols include, but are not limited to, methanol, ethanol, 1-propanol, 1-butanol, 2-methyl-1-propanol, 1-pentanol, 1-hexanol, 1-octanol, 1-decanol, 1-hexadecanol, 2-buten-1-ol, ethylene glycol, trimethylene glycol, glycerol, hexamethylene glycol, pentaerythritol, and other saturated or unsaturated aliphatic primary alcohols each containing from about 1 to about 30, preferably from about 1 to about 20, and more preferably from about 1 to about 15 carbon atoms; cyclopentylmethyl alcohol, cyclohexylmethyl alcohol, 2-cyclohexylethyl alcohol, and other saturated or unsaturated alicyclic primary alcohols; benzyl alcohol, 1,2-(1,3-or 1,4-)bis(hydroxymethyl)benzene, 1,2,3-(1,2,4-or 1,3,5-)tris(hydroxymethyl)benzene, 2-phenylethyl alcohol, 3-phenylpropyl alcohol, cinnamic alcohol, and other aromatic primary alcohols; and 2-hydroxymethylpyridine, and other heterocyclic primary alcohols. Primary alcohols each having at least one substituent on its hydrocarbon moiety include, but are not limited to, methyl glycolate, ethyl glycolate, and other glycolic esters; ethylene glycol monomethyl ether, ethylene glycol monoethyl ether, and other alkylene glycol monoalkyl ethers; ethylene glycol monoacetate, and other alkylene glycol monoesters.

Typical secondary alcohols include, but are not limited to, 2-propanol, s-butyl alcohol, 2-pentanol, 3-pentanol, 3,3-dimethyl-2-butanol, 2-octanol, 4-decanol, 2-hexadecanol, 2-penten-4-ol, glycerol, 1,2-propanediol, 2,3-butanediol, 2,3-pentanediol, and other vicinal diols, and other saturated or unsaturated aliphatic secondary alcohols each containing from about 3 to about 30, preferably from about 3 to about 20, and more preferably from about 3 to about 15 carbon atoms; 1-cyclopentylethanol, 1-cyclohexylethanol, and other secondary alcohols each having an aliphatic hydrocarbon group and an alicyclic hydrocarbon (e.g., a cycloalkyl group) combined with a carbon atom that is combined with a hydroxyl group; cyclobutanol, cyclopentanol, cyclohexanol, cyclooctanol, cyclododecanol, 2-cyclohepten-1-ol, 2-cyclohexen-1-ol, 2-adamantanol, 2-adamantanols each having an oxo group on its adamantane ring, 2-hydroxynorbornane, 2,5-dihydroxynorbornane, 3-hydroxytetracyclo[4.4.0.1$^{2,5}$.1$^{7,10}$]dodecane, and other saturated or unsaturated alicyclic secondary alcohols (including bridged secondary alcohols) each containing from about 3 to about 20 members, preferably from about 3 to about 15 members, more preferably from about 5 to about 15 members, and typically from about 5 to about 8 members; 1-phenylethanol, 1-phenylpropanol, 1-phenylmethylethanol, diphenylmethanol, and other aromatic secondary alcohols; and 1-(2-pyridyl)ethanol, and other heterocyclic secondary alcohols.

Typical tertiary alcohols include, but are not limited to, t-butyl alcohol, t-amyl alcohol, and other substituted or unsubstituted aliphatic tertiary alcohols each containing from about 4 to about 30, preferably from about 4 to about 20, and more preferably from about 4 to about 15 carbon atoms; 1-cyclohexyl-1-methylethanol, and other secondary alcohols each containing an aliphatic hydrocarbon group and an alicyclic hydrocarbon group (e.g., a cycloalkyl group and a bridged hydrocarbon group) combined with a carbon atom with which a hydroxyl group is combined; 1-methyl-1-cyclohexanol, and other tertiary alcohols each containing a hydroxyl group and an aliphatic hydrocarbon group combined with one carbon atom constituting an alicyclic ring (e.g., a cycloalkane ring, and a bridged carbon ring); 1-adamantanol, and other bridged carbon ring-containing tertiary alcohols each containing a hydroxyl group at a bridgehead position of a bridged carbon ring; 1-phenyl-1-methylethanol, and other aromatic tertiary alcohols; 1-methyl-1-(2-pyridyl)ethanol, and other heterocyclic tertiary alcohols.

Typical phenols include, but are not limited to, phenol, cresol, hydroquinone, resorcinol, catechol, 1-hydroxynaphthalene, and other compounds each containing a hydroxyl group combined with an aromatic carbon ring; 2-hydroxypyridine, 3-hydroxypyridine, 4-hydroxypyridine, 3-hydroxyfuran,-3-hydroxythiophene, and other compounds each containing a hydroxyl group combined with an aromatic heterocyclic ring. These hydroxy compounds may each have at least one substituent within a range not deteriorating the reaction.

In addition to the above-exemplified compounds, preferred hydroxy compounds also include compounds represented by following Formula (13):

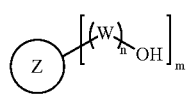

(13)

wherein ring Z is any one of cyclic groups represented by following Formulae (5) through (12):

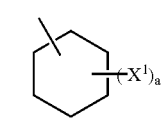

(5)

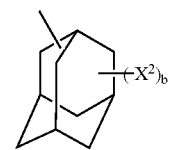

(6)

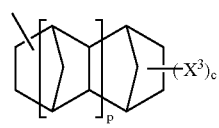

(7)

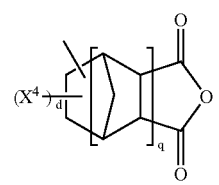

(8)

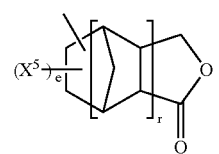

(9)

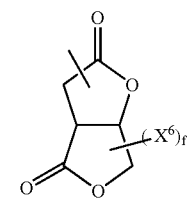

(10)

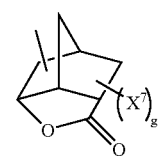

(11)

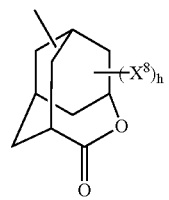

(12)

wherein $X^1$, $X^2$, $X^3$, $X^4$, $X^5$, $X^6$, $X^7$, and $X^8$ are each a substituent combined with an atom constituting each ring and are each a halogen atom, an alkyl group, a haloalkyl group, an aryl group, a hydroxyl group which may be protected by a protecting group, a hydroxymethyl group which may be protected by a protecting group, an amino group which may be protected by a protecting group, a carboxyl group which may be protected by a protecting group, a sulfo group which may be protected by a protecting group, an oxo group, a nitro group, a cyano group, or an acyl group which may be protected by a protecting group, wherein, when there are two or more substituents $X^1$s, these $X^1$s may be combined to form a ring containing four or more members with a carbon atom constituting the cyclohexane ring in Formula (5);

a, b, C, d, e, f, g, and h are each an integer of 0 or more, wherein substituents in the parentheses may be the same or different when a, b, c, d, e, f, g or h is 2 or more; and p, q, and r are each an integer of from 0 to 3;

W is a divalent hydrocarbon group;

n is 0 or 1;

m is an integer from 1 to 8;

wherein groups in the parentheses may be the same or different when m is 2 or more;

wherein a in Formula (5) is 1 or more and b in Formula (6) is 1 or more when n is 0 and m is 1; and wherein, in Formula (7), c is 1 or more when p is 0 or 1, and $X^3$ is a group other than hydroxyl group when p is 0 and c is 1.

The groups $X^1$, $X^2$, $X^3$, $X^4$, $X^5$, $X^6$, $X^7$, and $X^8$ are each a substituent combined with an atom constituting each ring. The ring just mentioned above means a ring indicated in the formulae, such as cyclohexane ring, adamantane ring, norbornane ring, tetracyclo[4.4.0.1$^{2,5}$1$^{7,10}$]dodecane ring, 4-oxatricyclo[5.2.1.0$^{2,6}$]decane-3,5-dione ring, γ-butyrolactone ring, 4-oxatricyclo[5.2.1.0$^{2,6}$]decan-3-one ring, 3-oxatricyclo[4.2.1.0$^{4,8}$]nonan-2-one ring, and 3-oxatricyclo[4.3.1.1$^{4,8}$]undecan-2-one ring. The halogen atom in $X^1$ and the other substituents includes, for example, fluorine, chlorine, and bromine atoms. The alkyl group in $X^1$ and the other substituents includes, but is not limited to, methyl, ethyl, propyl, isopropyl, butyl, isobutyl, s-butyl, t-butyl, hexyl, octyl, decyl, and other $C_1$–$C_{10}$ alkyl groups, of which $C_1$–$C_5$ alkyl groups are preferred. The haloalkyl group in $X^1$ and the other substituents includes, but is not limited to, chloromethyl, trifluoromethyl, trifluoroethyl, pentafluoroethyl, and other $C_1$–$C_{10}$ haloalkyl groups, of which $C_1$–$C_5$ haloalkyl groups are preferred. The aryl group in $X^1$ and the other substituents includes, but is not limited to, phenyl, and naphthyl groups. The aromatic rings of these aryl groups may each have at least one substituent. Such substituents include, for example, fluorine atom, and other halogen atoms; methyl group, and other $C_1$–$C_4$ alkyl groups; trifluoromethyl group, and other $C_1$–$C_5$ haloalkyl groups; hydroxyl group; methoxy group, and other $C_1$–$C_4$ alkoxy groups; amino group; dialkylamino groups; carboxyl group; methoxycarbonyl group, and other alkoxycarbonyl groups; nitro group; cyano group; acetyl group, and other acyl groups.

Hydroxyl- and hydroxymethyl-protecting groups in $X^1$ and the other substituents include protecting groups conventionally used in the field of organic synthesis. Such protecting groups include, but are not limited to, alkyl groups (e.g., methyl, t-butyl, and other $C_1$–$C_4$ alkyl groups), alkenyl groups (e.g., allyl group), cycloalkyl groups (e.g., cyclohexyl group), aryl groups (e.g., 2,4-dinitrophenyl group), aralkyl groups (e.g., benzyl group); substituted methyl groups (e.g., methoxymethyl, methylthiomethyl, benzyloxymethyl, t-butoxymethyl, and 2-methoxyethoxymethyl groups), substituted ethyl groups (e.g., 1-ethoxyethyl group), tetrahydropyranyl group, tetrahydrofuranyl group, 1-hydroxyalkyl groups (e.g., 1-hydroxyethyl group), and other groups capable of forming an acetal or hemiacetal group with a hydroxyl group; acyl groups (e.g., formyl, acetyl, propionyl, butyryl, isobutyryl, and pivaloyl, and other $C_1$–$C_6$ aliphatic acyl groups; acetoacetyl group; benzoyl, and other aromatic acyl groups), alkoxycarbonyl groups (e.g., methoxycarbonyl, and other $C_1$–$C_4$-alkoxycarbonyl groups), aralkyloxycarbonyl groups, substituted or unsubstituted carbamoyl groups, substituted silyl groups (e.g., trimethylsilyl group). When the molecule in question has two or more hydroxyl groups (inclusive of hydroxymethyl groups), the protecting groups also include, for example, divalent hydrocarbon groups (e.g., methylene, ethylidene, isopropylidene, cyclopentylidene, cyclohexylidene, and benzylidene groups) each of which may have at least one substituent.

Amino-protecting groups in $X^1$ and the other substituents include, for example, the alkyl groups, aralkyl groups, acyl groups, and alkoxycarbonyl groups exemplified as the hydroxyl-protecting groups.

Carboxy-protecting and sulfo-protecting groups in $X^1$ and the other substituents include, but are not limited to, alkoxy groups (e.g., methoxy, ethoxy, butoxy, and other $C_1$–$C_6$ alkoxy groups), cycloalkyloxy groups, aryloxy groups, aralkyloxy groups, trialkylsilyloxy groups, amino groups which may have at least one substituent, hydrazino group, alkoxycarbonylhydrazino groups, and aralkylcarbonylhydrazino groups.

The acyl group in $X^1$ and the other substituents includes, but is not limited to, formyl, acetyl, propionyl, butyryl, isobutyryl, pivaloyl, and other $C_1$–$C_6$ aliphatic acyl groups; acetoacetyl group; benzoyl, and other aromatic acyl groups. Acyl-protecting groups for use herein include protecting groups conventionally used in the field of organic synthesis. Such protected acyl groups include, for example, acetals inclusive of hemiacetals.

When the cyclohexane ring in Formula (5) has two or more $X^1$s, these $X^1$s may be combined to form a ring having four or more members with a carbon atom constituting the cyclohexane ring. Such rings include, but are not limited to, cyclopentane ring, cyclohexane ring, perhydronaphthalene ring (decalin ring), and other alicyclic carbon rings; γ-butyrolactone ring, δ-valerolactone ring, and other lactone rings.

The repetition numbers a, b, c, d, e, f, g, and h are each an integer of, for example, from 0 to 5, and preferably from 0 to 3.

W is a divalent hydrocarbon group. Such divalent hydrocarbon groups include divalent aliphatic hydrocarbon groups, divalent alicyclic hydrocarbon groups, divalent aromatic hydrocarbon groups, and hydrocarbon groups each comprising two or more of these groups combined with each other. These hydrocarbon groups may each have one or more monovalent hydrocarbon groups combined therewith. Such monovalent hydrocarbon groups include aliphatic hydrocarbon groups, alicyclic hydrocarbon groups, aromatic hydrocarbon groups, and hydrocarbon groups each comprising two or more of these groups combined with each other. The divalent hydrocarbon groups also include hydrocarbon groups each having at least one substituent. Such substituents include those exemplified in $X^1$ and the other substituents in ring Z.

Typical divalent hydrocarbon groups include, but are not limited to, methylene, methylmethylene, ethylmethylene, dimethylmethylene, ethylmethylmethylene, ethylene, trimethylene, tetramethylene, and other alkylene groups; propenylene, and other alkenylene groups; 1,3-cyclopentylene, 1,2-cyclohexylene, 1,3-cyclohexylene, 1,4-cyclohexylene, and other cycloalkylene groups; cyclopropylidene, cyclopentylidene, cyclohexylidene, and other cycloalkylidene groups; phenylene, and other arylene groups; and benzylidene group.

Preferred examples of W include groups represented by following Formula (14):

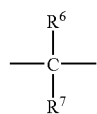
(14)

wherein $R^6$ and $R^7$ are the same or different and are each a hydrogen atom or a hydrocarbon group, and wherein $R^6$ and $R^7$ may be combined to form an alicyclic ring with the adjacent carbon atom.

Such hydrocarbon groups in $R^6$ and $R^7$ include hydrocarbon groups similar to those exemplified in $R^1$ and the other substituents. The hydrocarbon groups also include hydrocarbon groups each having at least one substituent. Such substituents include substituents similar to those which the hydrocarbon groups in $R^1$ and the other substituents may have, as well as substituents similar to $X^1$ and the other substituents in ring Z.

Preferred $R^6$ and $R^7$ include hydrogen atom; methyl, ethyl, propyl, isopropyl, butyl, and other $C_1$–$C_{10}$ alkyl groups, of which $C_1$–$C_5$ alkyl groups are typically preferred; cyclopentyl, cyclohexyl, and other substituted or unsubstituted cycloalkyl groups; norborn-2-yl, adamant-1-yl, and other substituted or unsubstituted bridged groups. Such substituents which the cycloalkyl groups and the bridged groups may have include substituents similar to $X^1$ and the other substituents in ring Z, such as halogen atoms, alkyl groups, haloalkyl groups, aryl groups, hydroxyl group which may be protected by a protecting group, hydroxymethyl group which may be protected by a protecting group, amino group which may be protected by a protecting group, carboxyl group which may be protected by a protecting group, sulfo group which may be protected by a protecting group, oxo group, nitro group, cyano group, and acyl groups which may be protected by a protecting group.

The repetition number m is an integer of preferably from 1 to 4, and more preferably from 1 to 3.

Typical examples of the hydroxy compounds represented by Formula (13) include the following compounds. The hydroxy compounds in which ring Z is a group represented by Formula (5) include, for example, cis-3,3,5-trimethyl-1-cyclohexanol, trans-3,3,5-trimethyl-1-cyclohexanol, 2-isopropyl-5-methyl-1-cyclohexanol (menthol), and 2-hydroxy-7-oxabicyclo[3.2.1]octan-6-one. Among these hydroxy compounds in which ring Z is a group represented by Formula (5), preference is given to compounds in which $X^1$ is a $C_1$–$C_5$ alkyl group, and the repetition number a is an integer of from 1 to 3, and to compounds in which two $X^1$s are combined to form an alicyclic ring or a lactone ring with a carbon atom constituting the cyclohexane ring in Formula (5).

The hydroxy compounds in which ring Z is a group represented by Formula (6) include, for example, 2-methyl-2-adamantanol, 2-ethyl-2-adamantanol, 1,3-adamantanediol, 1,3,5-adamantanetriol, 1,3,5,7-adamantanetetraol, 3,5-dimethyl-1-adamantanol, 5,7-dimethyl-1,3-adamantanediol, 3-carboxy-1-adamantanol, 3-amino-1-adamantanol, 3-nitro-1-adamantanol, 3-sulfo-1-adamantanol, 3-t-butyloxycarbonyl-1-adamantanol, 4-oxo-1-adamantanol, 3-hydroxy-α,α-dimethyl-1-adamantanemethanol, 1-adamantanemethanol, α,α-dimethyl-1-adamantanemethanol, α-ethyl-α-methyl-1-adamantanemethanol, α,α,α',α'-tetramethyl-1,3-adamantanedimethanol, and α-methyl-α-(norborn-2-yl)-1-adamantanemethanol. Among these hydroxy compounds in which ring Z is a group represented by Formula (6), preference is given to compounds in which m is 2 or 3, to compounds in which n is 1, and to compounds in which b is an integer of from 1 to 3.

The hydroxy compounds in which ring Z is a group represented by Formula (7) include, for example, 2,5-norbornanediol, 2,3-norbornanediol, 5-methoxycarbonyl-2-hydroxynorbornane, α-methyl-α-(norborn-2-yl)-2-norbornanemethanol, 2-norbornanemethanol, α,α-dimethyl-2-norbornanemethanol, α-butyl-α-methyl-2-norbornanemethanol, 3,4-dihydroxytetracyclo[4.4.0.1$^{2,5}$.1$^{7,10}$]dodecane, 3,8-dihydroxytetracyclo[4.4.0.1$^{2,5}$.1$^{7,10}$]dodecane, 3-hydroxy-8-methoxycarbonyltetracyclo[4.4.0.1$^{2,5}$.1$^{7,10}$]dodecane, 3-hydroxy-9-methoxycarbonyltetracyclo[4.4.0.1$^{2,5}$.1$^{7,10}$]dodecane, 3-tetracyclo[4.4.0.1$^{2,5}$.1$^{7,10}$]dodecanemethanol, 8-hydroxy-3-tetracyclo[4.4.0.1$^{2,5}$.1$^{7,10}$]dodecanemethanol, and 9-hydroxy-3-tetracyclo[4.4.0.1$^{2,5}$.1$^{7,10}$]dodecanemethanol.

Among these hydroxy compounds in which ring Z is a group represented by Formula (7), preference is given to compounds in which p is 0 and c is an integer of from 2 to 4, to compounds in which p is 0 and n is 1, to compounds in which p is 1 and c is an integer of from 1 to 4, and to compounds in which p is 0, c is 1 and $X^3$ is a group other than hydroxyl group.

The hydroxy compounds in which ring Z is a group represented by Formula (8) include, for example, 8-hydroxy-4-oxatricyclo[5.2.1.0$^{2,6}$]decane-3,5-dione, and 4-hydroxy-11-oxapentacyclo[6.5.1.1$^{3,6}$.0$^{2,7}$.0$^{9,13}$]pentadecane-10,12-dione.

The hydroxy compounds in which ring Z is a group represented by Formula (9) include, for example, α-hydroxy-γ,γ-dimethyl-γ-butyrolactone, α-hydroxy-α,γ,γ-trimethyl-γ-butyrolactone, α-hydroxy-γ,γ-dimethyl-β-methoxycarbonyl-γ-butyrolactone, 8-hydroxy-4-oxatricyclo[5.2.1.0$^{2,6}$]decan-3-one, 9-hydroxy-4-oxatricyclo[5.2.1.0$^{2,6}$]decan-3-one, and 8,9-dihydroxy-4-oxatricyclo[5.2.1.0$^{2,6}$]decan-3-one.

The hydroxy compounds in which ring Z is a group represented by Formula (10) include, for example, 4-hydroxy-2,7-dioxabicyclo[3.3.0]octane-3,6-dione.

The hydroxy compounds in which ring Z is a group represented by Formula (11) include, for example, 5-hydroxy-3-oxatricyclo[4.2.1.0$^{4,8}$]nonan-2-one, 5-hydroxy-5-methyl-3-oxatricyclo[4.2.1.0$^{4,8}$]nonan-2-one, and 5-hydroxy-9-methyl-3-oxatricyclo[4.2.1.0$^{4,8}$]nonan-2-one.

The hydroxy compounds in which ring Z is a group represented by Formula (12) include, for example, 6-hydroxy-3-oxatricyclo[4.3.1.1$^{4,8}$]undecan-2-one, and 6,8-dihydroxy-3-oxatricyclo[4.3.1.1$^{4,8}$]undecan-2-one.

Reactions

The reaction between the vinyl ester compound represented by Formula (1) and the hydroxy compound represented by Formula (2) is performed in the presence of, or in the absence of, a solvent. Such solvents include, but are not limited to, hexane, heptane, octane, and other aliphatic hydrocarbons; cyclohexane, and other alicyclic hydrocarbons; benzene, toluene, xylene, ethylbenzene, and other aromatic hydrocarbons; chloroform, dichloromethane, 1,2-dichloroethane, and other halogenated hydrocarbons; diethyl ether, dimethoxyethane, tetrahydrofuran, dioxane, and other ethers; acetone, methyl ethyl ketone, and other ketones; methyl acetate, ethyl acetate, isopropyl acetate, butyl acetate, and other esters; N,N-dimethylformamide, N,N-dimethylacetamide, and other amides; acetonitrile, propionitrile, benzonitrile, and other nitrites. Each of these solvents can be used alone or in combination.

The amount of the vinyl ester compound represented by Formula (1) is, for example, from about 0.8 to about 10 equivalents, preferably from about 1 to about 8 equivalents, and more preferably from about 1.5 to about 5 equivalents per equivalent of the hydroxy compound represented by Formula (2). It is also acceptable that the vinyl ester compound represented by Formula (1) is used in large excess.

By performing the reaction in the presence of a base, the reaction rate is markedly increased in most cases. Such bases include inorganic bases and organic bases. Such inorganic bases include, but are not limited to, lithium hydroxide, sodium hydroxide, potassium hydroxide, cesium hydroxide, and other alkali metal hydroxides; magnesium hydroxide, calcium hydroxide, barium hydroxide, and other alkaline earth metal hydroxides; lithium carbonate, sodium carbonate, potassium carbonate, cesium carbonate, and other alkali metal carbonates; magnesium carbonate, and other alkaline earth metal carbonates; and lithium hydrogencarbonate, sodium hydrogencarbonate, potassium hydrogencarbonate, cesium hydrogencarbonate, and other alkali metal hydrogencarbonates.

The organic bases include, but are not limited to, lithium acetate, sodium acetate, potassium acetate, cesium acetate, and other organic acid salts of alkali metals (in particular, alkali metal acetates); magnesium acetate, and other organic acid salts of alkaline earth metals; lithium methoxide, sodium methoxide, sodium ethoxide, sodium isopropoxide, potassium ethoxide, and other alkali metal alkoxides including alkali metal alkoxides corresponding to the hydroxy compounds represented by Formula (2); sodium phenoxide, and other alkali metal phenoxides; triethylamine, N-methylpiperidine, and other amines including tertiary amines; pyridine, 2,2'-bipyridyl, 1,10-phenanthroline, and other nitrogen-containing aromatic heterocyclic compounds. Among these bases, preference is given to those containing sodium.

The amount of the base is, for example, from about 0.001 to about 3 moles, and preferably from about 0.005 to 2 moles per mole of the hydroxy compound represented by Formula (2).

The reaction may be performed in the presence of a polymerization inhibitor. A reaction temperature can appropriately be selected depending on the types of the reaction components and the catalyst and is, for example, from about 20° C. to about 200° C., preferably from about 50° C. to about 150° C., and more preferably from about 70° C. to 120° C. The reaction can be performed at ordinary pressure (ambient pressure), under a reduced pressure, or under a pressure (under a load). The atmosphere of the reaction is not specifically limited as long as it does not adversely affect the reaction and includes, for example, an atmosphere of the air, of nitrogen gas, or of argon gas. The reaction can be performed in any system such as batch system, semi-batch system and continuous system.

The process of the present invention can yield a corresponding vinyl ether compound represented by Formula (3) under mild conditions as a result of the reaction. After the completion of the reaction, the reaction product can be separated and purified, for example, by filtration, concentration, distillation, extraction, crystallization, recrystallization, column chromatography, or another separation means or any combination of these separation means.

Vinyl Ether Compounds

The process of the present invention can yield the novel vinyl ether compounds represented by Formula (4). Specifically, the compound represented by Formula (4) can be obtained by allowing the vinyl ester compound represented by Formula (1) to react with the hydroxy compound represented by Formula (13) in the presence of a transition element compound.

In Formula (4), ring Z, W, n, m, and other symbols have the same meanings and are exemplified in the same manner as in Formula (13). In addition, $R^2$, $R^3$ and $R^4$ in Formula (4) have the same meanings and are exemplified in the same manner as in Formula (1).

Typical examples of the vinyl ether compounds represented by Formula (4) include the following compounds. Specifically, the vinyl ether compounds in which ring Z is a group represented by Formula (5) include, for example, cis-1,1,3-trimethyl-5-vinyloxycyclohexane, trans-1,1,3-trimethyl-5-vinyloxycyclohexane, 1-isopropyl-4-methyl-2-vinyloxycyclohexane, 2-vinyloxy-7-oxabicyclo[3.2.1]octan-6-one, and isopropenyl ethers corresponding to these compounds. Among these vinyl ether compounds in which ring Z is a group represented by Formula (5), preference is given to compounds in which $X^1$ is a $C_1$–$C_5$ alkyl group and a is an integer of from 1 to 3 and to compounds in which two $X^1$s are combined to form an alicyclic ring or a lactone ring with a carbon atom constituting the cyclohexane ring in Formula (5).

The vinyl ether compounds in which ring Z is a group represented by Formula (6) include, for example, 2-methyl-2-vinyloxyadamantane, 2-ethyl-2-vinyloxyadamantane, 1,3-bis(vinyloxy)adamantane, 3-vinyloxy-1-adamantanol, 1,3,5-tris(vinyloxy)adamantane, 3,5-bis(vinyloxy)-1-adamantanol, 5-vinyloxy-1,3-adamantanediol, 1,3,5,7-tetrakis(vinyloxy)adamantane, 3,5,7-tris(vinyloxy)-1-adamantanol, 5,7-bis(vinyloxy)-1,3-adamantanediol, 7-vinyloxy-1,3,5-adamantanetriol, 1,3-dimethyl-5-vinyloxyadamantane, 1,3-dimethyl-5,7-bis(vinyloxy)adamantane, 3,5-dimethyl-7-vinyloxy-1-adamantanol, 1-carboxy-3-vinyloxyadamantane, 1-amino-3-vinyloxyadamantane, 1-nitro-3-vinyloxyadamantane, 1-sulfo-3-vinyloxyadamantane, 1-t-butyloxycarbonyl-3-vinyloxyadamantane, 4-oxo-1-vinyloxyadamantane, 1-vinyloxy-3-(1-methyl-1-vinyloxyethyl)adamantane, 1-(vinyloxymethyl)adamantane, 1-(1-methyl-1-vinyloxyethyl)adamantane, 1-(1-ethyl-1-vinyloxyethyl)adamantane, 1,3-bis(1-methyl-1-vinyloxyethyl)adamantane, 1-(1-(norborn-2-yl)-1-vinyloxyethyl) adamantane, and isopropenyl ethers corresponding to these compounds. Among these vinyl ether compounds in which ring Z is a group represented by Formula (6), preference is given to compounds in which m is 2 or 3, to compounds in which n is 1, and to compound in which b is an integer of from 1 to 3.

The vinyl ether compounds in which ring Z is a group represented by Formula (7) include, for example, 2,5-bis (vinyloxy)norbornane, 2,3-bis(vinyloxy)norbornane, 5-methoxycarbonyl-2-vinyloxynorbornane, 2-(1-(norborn-2-yl)-1-vinyloxyethyl)norbornane, 2-(vinyloxymethyl)norbornane, 2-(1-methyl-1-vinyloxyethyl)norbornane, 2-(1-methyl-1-vinyloxypentyl)norbornane, 3-hydroxy-4-vinyloxytetracyclo[4.4.0.1$^{2,5}$.1$^{10}$]dodecane, 3,4-bis (vinyloxy)tetracyclo[4.4.0.1$^{2,5}$.1$^{7,10}$]dodecane, 3-hydroxy-8-vinyloxytetracyclo[4.4.0.1$^{2,5}$.1$^{7,10}$]dodecane, 3,8-bis (vinyloxy)tetracyclo[4.4.0.1$^{2,5}$.1$^{7,10}$]dodecane, 3-methoxycarbonyl-8-vinyloxytetracyclo[4.4.0.1$^{2,5}$.1$^{7,10}$] dodecane, 3-methoxycarbonyl-9-vinyloxytetracyclo

[4.4.0.1$^{2,5}$.1$^{7,10}$]dodecane, 3-(vinyloxymethyl)tetracyclo[4.4.0.1$^{2,5}$.1$^{7,10}$]dodecane, 3-hydroxymethyl-8-vinyloxytetracyclo[4.4.0.1$^{2,5}$.1$^{7,10}$]dodecane, 3-hydroxymethyl-9-vinyloxytetracyclo[4.4.0.1$^{2,5}$.1$^{7,10}$]dodecane, 8-hydroxy-3-(vinyloxymethyl)tetracyclo[4.4.0.1$^{2,5}$.1$^{7,10}$]dodecane, 9-hydroxy-3-(vinyloxymethyl)tetracyclo[4.4.0.1$^{2,5}$.1$^{7,10}$]dodecane, and isopropenyl ethers corresponding to these compounds. Among these vinyl ether compounds in which ring Z is a group represented by Formula (7), preference is given to compounds in which p is 0 and c is an integer of from 2 to 4, to compounds in which p is 0 and n is 1, to compounds in which p is 1 and c is an integer of from 1 to 4, and to compounds in which p is 0, c is 1 and X$^3$ is a group other than hydroxyl group.

The vinyl ether compounds in which ring Z is a group represented by Formula (8) include, for example, 8-vinyloxy-4-oxatricyclo[5.2.1.0$^{2,6}$]decane-3,5-dione, 4-vinyloxy-11-oxapentacyclo[6.5.1.1$^{3,6}$.0$^{2,7}$.0$^{9,13}$]pentadecane-10,12-dione, and isopropenyl ethers corresponding to these compounds.

The vinyl ether compounds in which ring Z is a group represented by Formula (9) include, for example, α-vinyloxy-γ,γ-dimethyl-γ-butyrolactone, α,γ,γ-trimethyl-α-vinyloxy-γ-butyrolactone, γ,γ-dimethyl-β-methoxycarbonyl-α-vinyloxy-γ-butyrolactone, 8-vinyloxy-4-oxatricyclo[5.2.1.0$^{2,6}$]decan-3-one, 9-vinyloxy-4-oxatricyclo[5.2.1.0$^{2,6}$]decan-3-one, 8,9-bis(vinyloxy)-4-oxatricyclo[5.2.1.0$^{2,6}$]decan-3-one, and isopropenyl ethers corresponding to these compounds.

The vinyl ether compounds in which ring Z is a group represented by Formula (10) include, for example, 4-vinyloxy-2,7-dioxabicyclo[3.3.0]octane-3,6-dione, and isopropenyl ethers corresponding to this compound.

The vinyl ether compounds in which ring Z is a group represented by Formula (11) include, for example, 5-vinyloxy-3-oxatricyclo[4.2.1.0$^{4,8}$]nonan-2-one, 5-methyl-5-vinyloxy-3-oxatricyclo[4.2.1.0$^{4,8}$]nonan-2-one, 9-methyl-5-vinyloxy-3-oxatricyclo[4.2.1.0$^{4,8}$]nonan-2-one, and isopropenyl ethers corresponding to these compounds.

The vinyl ether compounds in which ring Z is a group represented by Formula (12) include, for example, 6-vinyloxy-3-oxatricyclo[4.2.1.0$^{4,8}$]undecan-2-one, 6,8-bis(vinyloxy)-3-oxatricyclo[4.2.1.0$^{4,8}$]undecan-2-one, 6-hydroxy-8-vinyloxy-3-oxatricyclo[4.2.1.0$^{4,8}$]undecan-2-one, 8-hydroxy-6-vinyloxy-3-oxatricyclo[4.2.1.0$^{4,8}$]undecan-2-one, and isopropenyl ethers corresponding to these compounds.

The vinyl ether compounds represented by Formula (4) of the present invention can be used as raw materials for pharmaceutical drugs, agricultural chemicals, and other fine chemicals, as well as raw materials for polymers such as resist resins, optical plastics, transparent resins, and crosslinking resins. In particular, they each have a non-aromatic cyclic skeleton such as an alicyclic skeleton or a lactone skeleton and are useful as material monomers for resist resins, since they can improve transparency and resistance to dry etching when they are used as comonomers of such polymers.

EXAMPLES

The present invention will be illustrated in further detail with reference to several examples below, which are not intended to limit the scope of the invention.

Example 1

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 98% with a conversion from 1-octanol of 100%.

Example 2

To a mixture of di-μ-chlorobis(1,5-cyclooctadiene)diiridium(I) [Ir(cod)Cl]$_2$ (6.7 g, 0.01 mol) and sodium carbonate (64 g, 0.6 mol) in toluene (1.0 L), 1-octanol (130 g, 1 mol) and vinyl acetate (172 g, 2 mol) were added, followed by stirring at 100° C. in an atmosphere of argon gas for 2 hours. The reaction mixture was cooled to room temperature, the resulting precipitated salt was filtrated, the filtrate was concentrated in an evaporator under a reduced pressure, the residue was distillated and thereby yielded 1-octyl vinyl ether.

Example 3

To a mixture of di-μ-chlorobis(1,5-cyclooctadiene)diiridium(I) [Ir(cod)Cl]$_2$ (6.7 mg, 0.01 mmol) and sodium carbonate (32 mg, 0.3 mmol) in toluene (1.0 ml), 1-octanol (130 mg, 1 mmol) and vinyl acetate (430 mg, 5 mmol) were added, followed by stirring at 100° C. in an atmosphere of argon gas for 2 hours. The reaction mixture was analyzed by gas chromatography to find that 1-octyl vinyl ether was produced in a yield of 82% with a conversion from 1-octanol of 100%.

Example 4

To a mixture of di-μ-chlorobis(1,5-cyclooctadiene)diiridium(I) [Ir(cod)Cl]$_2$ (6.7 mg, 0.01 mmol) and sodium carbonate (1.1 mg, 0.01 mmol) in toluene (1.0 ml), 1-octanol (130 mg, 1 mmol) and vinyl acetate (430 mg, 5 mmol) were added, followed by stirring at 100° C. in an atmosphere of argon gas for 2 hours. The reaction mixture was analyzed by gas chromatography to find that 1-octyl vinyl ether was produced in a yield of 67% with a conversion from 1-octanol of 86%.

Example 5

To a mixture of di-μ-chlorobis(1,5-cyclooctadiene)diiridium(I) [Ir(cod)Cl]$_2$ (6.7 mg, 0.01 mmol) and toluene (1.0 ml), 1-octanol (130 mg, 1 mmol) and vinyl acetate (430 mg, 5 mmol) were added, followed by stirring at 100° C. in an atmosphere of argon gas for 2 hours. The reaction mixture was analyzed by gas chromatography to find that 1-octyl vinyl ether was produced in a yield of 1% with a conversion from 1-octanol of 3%.

Example 6

To a mixture of di-μ-chlorobis(1,5-cyclooctadiene)diiridium(I) [Ir(cod)Cl]$_2$ (6.7 mg, 0.01 mmol) and sodium acetate (49 mg, 0.6 mmol) in toluene (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 82% with a conversion from 1-octanol of 100%.

Example 7

To a mixture of di-μ-chlorobis(1,5-cyclooctadiene)diiridium(I) [Ir(cod)Cl]$_2$ (6.7 mg, 0.01 mmol) and potassium carbonate (83 mg, 0.6 mmol) in toluene (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 3% with a conversion from 1-octanol of 39%.

Example 8

To a mixture of di-μ-chlorobis(1,5-cyclooctadiene)diiridium(I) [Ir(cod)Cl]$_2$ (6.7 mg, 0.01 mmol) and cesium carbonate (195 mg, 0.6 mmol) in toluene (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 6% with a conversion from 1-octanol of 30%.

Example 9

To a mixture of di-μ-chlorobis(1,5-cyclooctadiene)diiridium(I) [Ir(cod)Cl]$_2$ (6.7 mg, 0.01 mmol) and pyridine (95 mg, 1.2 mmol) in toluene (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 1% with a conversion from 1-octanol of 2%.

Example 10

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1-octanol (130 mg, 1 mmol) and vinyl acetate (172 mg, 2 mmol) were added, followed by stirring at 90° C. in an atmosphere of argon gas for 3 hours. The reaction mixture was analyzed by gas chromatography to find that 1-octyl vinyl ether was produced in a yield of 98% with a conversion from 1-octanol of 100%.

Example 11

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1-octanol (130 mg, 1 mmol) and vinyl acetate (172 mg, 2 mmol) were added, followed by stirring at 80° C. in an atmosphere of argon gas for 2 hours. The reaction mixture was analyzed by gas chromatography to find that 1-octyl vinyl ether was produced in a yield of 55% with a conversion from 1-octanol of 58%.

Example 12

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in 1,4-dioxane (1.0 ml), 1-octanol (130 mg, 1 mmol) and vinyl acetate (172 mg, 2 mmol) were added, followed by stirring at 100° C. in an atmosphere of argon gas for 2 hours. The reaction mixture was analyzed by gas chromatography to find that 1-octyl vinyl ether was produced in a yield of 84% with a conversion from 1-octanol of 85%.

Example 13

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), benzyl alcohol (108 mg, 1 mmol) and vinyl acetate (172 mg, 2 mmol) were added, followed by stirring at 100° C. in an atmosphere of argon gas for 2 hours. The reaction mixture was analyzed by gas chromatography to find that benzyl vinyl ether was produced in a yield of 94% with a conversion from benzyl alcohol of 100%.

Example 14

To a mixture of di-μ-chlorobis(1,5-cyclooctadiene)diiridium(I) [Ir(cod)Cl]2 (6.7 mg, 0.01 mmol) and sodium carbonate (64 mg, 0.6 mmol) in toluene (1.0 ml), 1,6-hexanediol (118 mg, 1 mmol) and vinyl acetate (344 mg, 4 mmol) were added, followed by stirring at 100° C. in an atmosphere of argon gas for 6 hours. The reaction mixture was analyzed by gas chromatography to find that 1,6-bis(vinyloxy)hexane and 6-vinyloxy-1-hexanol were produced in yields of 87% and 2%, respectively, with a conversion from 1,6-hexanediol of 97%.

Example 15

To a mixture of di-μ-chlorobis(1,5-cyclooctadiene)diiridium(I) [Ir(cod)Cl ]$_2$ (6.7 mg, 0.01 mmol) and sodium carbonate (64 mg, 0.6 mmol) in toluene (1.0 ml), sec-phenethyl alcohol (1-phenylethyl alcohol) (122 mg, 1 mmol) and vinyl acetate (172 mg, 2 mmol) were added, followed by stirring at 100° C. in an atmosphere of argon gas for 2 hours. The reaction mixture was analyzed by gas chromatography to find that sec-phenethyl vinyl ether was produced in a yield of 95% with a conversion from sec-phenethyl alcohol of 97%.

Example 16

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1-adamantanol (152 mg, 1 mmol) and vinyl acetate (258 mg, 3 mmol) were added, followed by stirring at 100° C. in an atmosphere of argon gas for 5 hours. The reaction mixture was analyzed by gas chromatography to find that 1-adamantyl vinyl ether and 1-(adamant-1-yloxy) ethyl acetate were produced in yields of 91% and 1%, respectively, with a conversion from 1-adamantanol of 93%.

[Spectral data of 1-adamantyl vinyl ether]
MS m/e: 178, 135, 93, 79, 41
$^1$H-NMR (CDCl$_3$, TMS) δ: 6.59 (dd, 1H), 4.29 (dd, 1H), 4.02 (dd, 1H), 2.18 (brs, 3H), 1.80–1.50 (m, 12H)

[Spectral data of 1-(adamant-1-yloxy)ethyl acetate]
$^1$H-NMR (CDCl$_3$, TMS) δ: 6.21 (q, 1H), 2.13 (brs, 3H), 2.02 (s, 3H), 1.90–1.50 (m, 12H), 1.35 (s, 3H)

Example 17

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), menthol (156 mg, 1 mmol) and vinyl acetate (172 mg, 2 mmol) were added, followed by stirring at 100° C. in an atmosphere of argon gas for 4 hours. The reaction mixture was analyzed by gas chromatography to find that 1-isopropyl-4-methyl-2-vinyloxycyclohexane was produced in a yield of 86% with a conversion from menthol of 89%.

[Spectral data of 1-isopropyl-4-methyl-2-vinyloxycyclohexane]

M/S m/e: 182, 139, 83, 69, 55,

Example 18

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), phenol (94 mg, 1 mmol) and vinyl acetate (172 mg, 2 mmol) were added, followed by stirring at 100° C. in an atmosphere of argon gas for 2 hours. The reaction mixture was analyzed by gas chromatography to find that phenyl vinyl ether was produced in a yield of 98% with a conversion from phenol of 100%.

Example 19

To a mixture of dichloro(1,5-cyclooctadiene)ruthenium [Ru(cod)Cl$_2$] (2.8 mg, 0.01 mmol) and sodium carbonate (64 mg, 0.6 mmol) in toluene (1.0 ml), phenol (94 mg, 1 mmol) and vinyl acetate (172 mg, 2 mmol) were added, followed by stirring at 100° C. in an atmosphere of argon gas for 5 hours. The reaction mixture was analyzed by gas chromatography to find that phenyl vinyl ether was produced in a yield of 65% with a conversion from phenol of 69%.

Example 20

To a mixture of dichloro(1,5-cyclooctadiene)platinum [Pt(cod)Cl$_2$] (3.7 mg, 0.01 mmol) and sodium carbonate (64 mg, 0.6 mmol) in toluene (1.0 ml), phenol (94 mg, 1 mmol) and vinyl acetate (172 mg, 2 mmol) were added, followed by stirring at 100° C. in an atmosphere of argon gas for 5 hours. The reaction mixture was analyzed by gas chromatography to find that phenyl vinyl ether was produced in a yield of 48% with a conversion from phenol of 52%.

Example 21

To a mixture of di-μ-chlorobis(1,5-cyclooctadiene)dirhodium [Rh(cod)Cl]$_2$ (4.9 mg, 0.01 mmol) and sodium carbonate (64 mg, 0.6 mmol) in toluene (1.0 ml), phenol (94 mg, 1 mmol) and vinyl acetate (172 mg, 2 mmol) were added, followed by stirring at 100° C. in an atmosphere of argon gas for 5 hours. The reaction mixture was analyzed by gas chromatography to find that phenyl vinyl ether was produced in a yield of 55% with a conversion from phenol of 58%.

Example 22

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), cis-3,3,5-trimethyl-1-cyclohexanol (1 mmol) and vinyl acetate (3 mmol) were added, followed by stirring at 100° C. in an atmosphere of argon gas for 5 hours. The reaction mixture was analyzed by gas chromatography to find that cis-1,1,3-trimethyl-5-vinyloxycyclohexane was produced in a yield of 91% with a conversion from cis-3,3,5-trimethyl-1-cyclohexanol of 95%.

[Spectral data of cis-1,1,3-trimethyl-5-vinyloxycyclohexane]

$^1$H-NMR (CDCl$_3$, TMS) δ: 6.51 (dd, 1H), 4.19 (dd, 1H), 4.00 (dd, 1H), 3.54 (m, 1H), 2.07–1.97 (m, 1H), 1.78–1.65 (m, 2H), 1.40–1.32 (m, 1H), 1.56 (dd, 1H), 0.96 (s, 3H), 0.90–0.78 (m, 2H), 0.93 (s, 3H), 0.91 (s, 3H)

Example 23

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1,3-adamantanediol (1 mmol) and vinyl acetate (6 mmol) were added, followed by stirring at 100° C. in an atmosphere of argon gas for 5 hours. The reaction mixture was analyzed by gas chromatography to find that 1,3-bis(vinyloxy)adamantane and 3-vinyloxy-1-adamantanol were produced in yields of 41% and 16%, respectively, with a conversion from 1,3-adamantanediol of 97%.

[Spectral data of 1,3-bis(vinyloxy)adamantane]

MS m/e: 220, 177, 135, 121, 93, 79, 77

[Spectral data of 3-vinyloxy-1-adamantanol]

MS m/e: 194, 151, 133, 95, 93, 41

Example 24

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1,3,5-adamantanetriol (1 mmol) and vinyl acetate (9 mmol) were added, followed by stirring at 100° C. in an atmosphere of argon gas for 5 hours. The reaction mixture was analyzed by gas chromatography to find that 1,3,5-tris(vinyloxy)adamantane, 3,5-bis(vinyloxy)-1-adamantanol, and 5-vinyloxy-1,3-adamantanediol were produced in yields of 52%, 18%, and 8%, respectively, with a conversion from 1,3,5-adamantanetriol of 97%.

[Spectral data of 1,3,5-tris(vinyloxy)adamantane]

MS m/e: 262, 135, 93, 41

[Spectral data of 3,5-bis(vinyloxy)-1-adamantanol]

MS m/e: 236, 135, 107, 41

[Spectral data of 5-vinyloxy-1,3-adamantanediol]

MS m/e: 210, 135, 91

Example 25

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 3-t-butyloxycarbonyl-1-adamantanol (1 mmol) and vinyl acetate (3 mmol) were added, followed by stirring at 100° C. in an atmosphere of argon gas for 5 hours. The reaction mixture was analyzed by gas chromatography to find that t-butyl 3-vinyloxyadamantane-1-carboxylate (i.e., 1-t-butyloxycarbonyl-3-vinyloxyadamantane) represented by following Formula (15) was produced in a yield of 82% with a conversion from 3-t-butyloxycarbonyl-1-adamantanol of 97%.

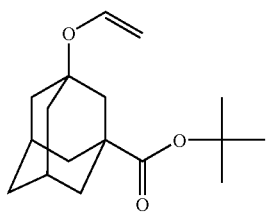

(15)

[Spectral data of t-butyl 3-vinyloxyadamantane-1-carboxylate]

MS m/e: 278, 135, 93, 41

Example 26

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 4-oxo-1-adamantanol (1 mmol) and vinyl acetate (3 mmol) were added, followed by stirring at 100° C. in an atmosphere of argon gas for 5 hours. The reaction mixture was analyzed by gas chromatography to find that 5-vinyloxyadamantan-2-one (i.e., 1-vinyloxy-4-oxoadamantane) represented by following Formula (16) was produced in a yield of 78% with a conversion from 4-oxo-1-adamantanol of 87%.

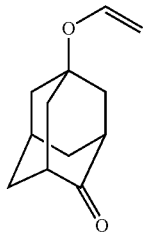

(16)

[Spectral data of 5-vinyloxyadamantan-2-one]

$^1$H-NMR (CDCl$_3$, TMS) δ: 6.68 (dd, 1H), 4.32 (dd, 1H), 4.08 (dd, 1H), 2.68 (brs, 2H), 2.52–2.30 (m, 7H), 2.12–1.87 (m, 4H)

Example 27

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 1-hydroxy-4-oxatricyclo[4.3.1.1$^{3,8}$]undecan-5-one (i.e., 6-hydroxy-3-oxatricyclo[4.3.1.1$^{3,8}$]undecan-2-one (1 mmol) and vinyl acetate (3 mmol) were added, followed by stirring at 100° C. in an atmosphere of argon gas for 5 hours. The reaction mixture was analyzed by gas chromatography to find that 1-vinyloxy-4-oxatricyclo[4.3.1.1$^{3,8}$]undecan-5-one (i.e., 6-vinyloxy-3-oxatricyclo[4.3.1.1$^{3,8}$]undecan-2-one) represented by following Formula (17) was produced in a yield of 72% with a conversion from 1-hydroxy-4-oxatricyclo[4.3.1.1$^{3,8}$]undecan-5-one of 82%.

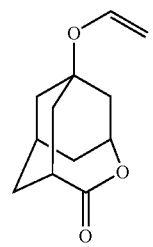

(17)

[Spectral data of 1-vinyloxy-4-oxatricyclo[4.3.1.1$^{3,8}$]undecan-5-one]

$^1$H-NMR (CDCl$_3$, TMS) δ: 6.62 (dd, 1H), 4.25 (dd, 1H), 4.01 (dd, 1H), 4.63 (m, 1H), 3.16 (m, 1H), 2.43 (m, 1H), 2.15–1.68 (m, 10H)

Example 28

To a mixture of di-μ-chlorobis(-1,5-cyclooctadiene)diiridium(I) [Ir(cod)Cl ]$_2$ (6.7 mg, 0.01 mmol) and sodium carbonate (64 mg, 0.6 mmol) in toluene (1.0 ml), α, α-dimethyl-1-adamantanemethanol (1 mmol) and vinyl acetate (3 mmol) were added, followed by stirring at 100° C. in an atmosphere of argon gas for 5 hours. The reaction mixture was analyzed by gas chromatography to find that 1-(1-methyl-1-vinyloxyethyl)adamantane represented by following Formula (18) was produced in a yield of 85% with a conversion from α,α-dimethyl-1-adamantanemethanol of 92%.

(18)

[Spectral data of 1-(1-methyl-1-vinyloxyethyl)adamantane]

$^1$H-NMR (CDCl$_3$, TMS) δ: 6.64 (dd, 1H), 4.30 (dd, 1H), 4.05 (dd, 1H), 2.05 (brs, 3H), 1.78–1.56 (m, 10H), 1.51 (s, 6H)

Example 29

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), α-hydroxy-γ,γ-dimethyl-γ-butyrolactone (1 mmol) and vinyl acetate (3 mmol) were added, followed by stirring at 100° C. in an atmosphere of argon gas for 5 hours. The reaction mixture was analyzed by gas chromatography to find that γ,γ-dimethyl-α-vinyloxy-γ-butyrolactone represented by following Formula (19) was produced in a yield of 92% with a conversion from α-hydroxy-γ,γ-dimethyl-γ-butyrolactone of 98%.

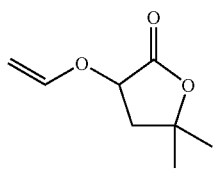

(19)

[Spectral data of γ, γ-dimethyl-α-vinyloxy-γ-butyrolactone]

$^1$H-NMR (CDCl$_3$, TMS) δ: 6.64 (dd, 1H), 4.30 (dd, 1H), 4.05 (dd, 1H), 5.66 (m, 1H), 2.68–2.58 (m, 1H), 2.18–2.02 (m, 1H), 1.54 (s, 3H), 1.47 (s, 3H)

Example 30

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), 5-hydroxy-3-oxatricyclo[4.2.1.0$^{4,8}$]nonan-2-one (i.e., 2-hydroxy-4-oxatricyclo[4.2.1.0$^{3,7}$]nonan-5-one) (1 mmol) and vinyl acetate (3 mmol) were added, followed by stirring at 100° C. in an atmosphere of argon gas for 5 hours. The reaction mixture was analyzed by gas chromatography to find that 5-vinyloxy-3-oxatricyclo[4.2.1.0$^{4,8}$]nonan-2-one (i.e., 2-vinyloxy-4-oxatricyclo[4.2.1.0$^{3,7}$]nonan-5-one) represented by following Formula (20) was produced in a yield of 96% with a conversion from 5-hydroxy-3-oxatricyclo[4.2.1.0$^{4,8}$]nonan-2-one of 98%.

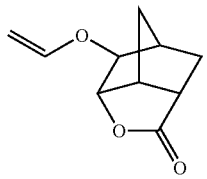

(20)

[Spectral data of 5-vinyloxy-3-oxatricyclo[4.2.1.0$^{4,8}$]nonan-2-one]

$^1$H-NMR (CDCl$_3$, TMS) δ: 6.52 (dd, 1H), 4.35 (dd, 1H), 4.03 (dd, 1H), 4.32 (d, 1H), 3.81 (m, 1H), 3.18 (m, 1H), 2.65–2.50 (m, 2H), 2.13–1.96 (m, 2H), 1.78 (ddd, 1H), 1.65 (ddd, 1H)

Example 31

To a mixture of di-μ-chlorobis(15-cyclooctadiene)diiridium(I) [Ir(cod)Cl]$_2$ (6.7 mg, 0.01 mmol) and sodium carbonate (64 mg, 0.6 mmol) in toluene (1.0 ml), 8,9-dihydroxy-4-oxatricyclo[5.2.1.0$^{2,6}$]decan-3-one (1 mmol) and vinyl acetate (6 mmol) were added, followed by stirring at 100° C. in an atmosphere of argon gas for 5 hours. The reaction mixture was analyzed by gas chromatography to find that 8,9-bis(vinyloxy)-4-oxatricyclo[5.2.1.0$^{2,6}$]decan-3-one represented by following Formula (21) was produced in a yield of 63% with a conversion from 8,9-dihydroxy-4-oxatricyclo[5.2.1.0$^{2,6}$]decan-3-one of 93%.

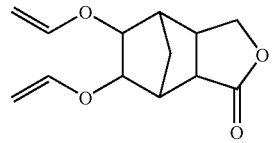

(21)

[Spectral data of 8,9-bis(vinyloxy)-4-oxatricyclo[5.2.1.0$^{2,6}$]decan-3-one]

MS m/e: 248, 138, 107, 79

Example 32

To a mixture of di-μ-chlorobis(1,5-cyclooctadiene)diiridium(I) [Ir(cod)Cl]$_2$ (6.7 mg, 0.01 mmol) and sodium carbonate (64 mg, 0.6 mmol) in toluene (1.0 ml), a mixture (1 mmol) of 3-hydroxy-8-methoxycarbonyltetracyclo[4.4.0.1$^{2,5}$.1$^{7,10}$]dodecane and 3-hydroxy-9-methoxycarbonyltetracyclo[4.4.0. 1$^{2,5}$.1$^{7,10}$]dodecane, and vinyl acetate (3 mmol) were added, followed by stirring at 100° C. in an atmosphere of argon gas for 5 hours. The reaction mixture was analyzed by gas chromatography to find that a mixture of 3-vinyloxy-8-methoxycarbonyltetracyclo[4.4.0.1$^{2,5}$.1$^{7,10}$]dodecane represented by following Formula (22) and 3-vinyloxy-9-methoxycarbonyltetracyclo[4.4.0.1$^{2,5}$.1$^{7,10}$]dodecane represented by following Formula (23) was produced in a total yield of 61% with a conversion from the mixture of 3-hydroxy-8-methoxycarbonyltetracyclo[4.4.0.1$^{2,5}$.1$^{7,10}$] dodecane and 3-hydroxy-9-methoxycarbonyltetracyclo [4.4.0.1$^{2,5}$.1$^{7,10}$]dodecane of 87%.

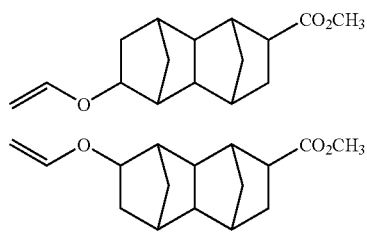

(22)

(23)

[Spectral data of a mixture of 3-vinyloxy-8-methoxycarbonyltetracyclo[4.4.0.1$^{2,5}$.1$^{7,10}$]dodecane and 3-vinyloxy-9-methoxycarbonyltetracyclo[4.4.0.1$^{2,5}$.1$^{7,10}$]dodecane]

MS m/e: 262, 218, 159, 81

Example 33

To a mixture of di-μ-chlorobis(1,5-cyclooctadiene)diiridium(I) [Ir(cod)Cl]$_2$ (0.01 mmol) and sodium carbonate (0.03 mmol) in toluene (1.0 ml), 1-octanol (130 mg, 1 mmol) and isopropenyl acetate (5 mmol) were added, followed by stirring at 100° C. in an atmosphere of argon gas for 15 hours. The reaction mixture was analyzed by gas chromatography to find that 1-octyl isopropenyl ether, 2,2-bis(1-octyloxy)propane, and octyl acetate were produced in yields of 78%, 4%, and 16%, respectively, with a conversion from 1-octanol of 98%.

Example 34

To a mixture of bis(1,5-cyclooctadiene)iridium tetrafluoroborate [Ir(cod)$_2$]$^+$BF$_4^-$ (0.01 mmol) and sodium carbonate (0.03 mmol) in toluene (1.0 ml), 1-octanol (130 mg, 1 mmol) and isopropenyl acetate (5 mmol) were added, followed by stirring at 100° C. in an atmosphere of argon gas for 15 hours. The reaction mixture was analyzed by gas chromatography to find that 1-octyl isopropenyl ether, 2,2-bis(1-octyloxy)propane, and octyl acetate were produced in yields of 67%, 6%, and 14%, respectively, with a conversion from 1-octanol of 93%.

Example 35

To a mixture of di-μ-chlorobis(1,5-cyclooctadiene)diiridium(I) [Ir(cod)Cl]$_2$ (0.01 mmol) and sodium carbonate (0.1 mmol) in toluene (1.0 ml), 1-octanol (130 mg, 1 mmol) and vinyl acetate (5 mmol) were added, followed by stirring at 100° C. in an atmosphere of argon gas for 2 hours. The reaction mixture was analyzed by gas chromatography to find that 1-octyl vinyl ether, octyl acetate, and 1-(1-octyloxy)ethyl acetate were produced in yields of 58%, 3%, and 21%, respectively, with a conversion from 1-octanol of 100%.

Example 36

To a mixture of di-μ-chlorobis(1,5-cyclooctadiene)diiridium(I) [Ir(cod)Cl]$_2$ (0.01 mmol) and sodium hydrogencarbonate (1.2 mmol) in toluene (1.0 ml), 1-octanol (130 mg, 1 mmol) and vinyl acetate (2 mmol) were added, followed by stirring at 100° C. in an atmosphere of argon gas for 2 hours. The reaction mixture was analyzed by gas chromatography to find that 1-octyl vinyl ether and octyl acetate were produced in yields of 93% and 2%, respectively, with a conversion from 1-octanol of 99%.

Example 37

To a mixture of bis(1,5-cyclooctadiene)iridium tetrafluoroborate [Ir(cod)$_2$]$^+$BF$_4^-$ (0.01 mmol) and sodium carbonate (0.6 mmol) in toluene (1.0 ml), 1-octanol (130 mg, 1 mmol) and vinyl acetate (2 mmol) were added, followed by stirring at 100° C. in an atmosphere of argon gas for 2 hours. The reaction mixture was analyzed by gas chromatography to find that 1-octyl vinyl ether and octyl acetate were produced in yields of 70% and 2%, respectively, with a conversion from 1-octanol of 72%.

Example 38

To a mixture of di-μ-chlorobis(1,5-cyclooctadiene)diiridium(I) [Ir(cod)Cl]$_2$ (0.01 mmol) and 4MgCO$_3$-Mg(OH)$_2$-5H$_2$O (0.6 mmol) in toluene (1.0 ml), 1-octanol (130 mg, 1 mmol) and vinyl acetate (2 mmol) were added, followed by stirring at 100° C. in an atmosphere of argon gas for 2 hours. The reaction mixture was analyzed by gas chromatography to find that 1-octyl vinyl ether and octyl acetate were produced in yields of 18% and 3%, respectively, with a conversion from 1-octanol of 44%.

Example 39

To a mixture of di-μ-chlorobis(1,5-cyclooctadiene)diiridium(I) [Ir(cod)Cl]$_2$ (0.01 mmol) and triethylamine (0.6 mmol) in toluene (1.0 ml), 1-octanol (130 mg, 1 mmol) and vinyl acetate (2 mmol) were added, followed by stirring at 100° C. in an atmosphere of argon gas for 2 hours. The reaction mixture was analyzed by gas chromatography to find that 1-octyl vinyl ether and octyl acetate were produced in yields of 19% and 2%, respectively, with a conversion from 1-octanol of 30%.

Example 40

To a mixture of (1,5-cyclooctadiene)(acetonitrile)iridium tetrafluoroborate [Ir(cod) (CH$_3$CN)]$^+$BF$_4^-$ (0.01 mmol) and sodium carbonate (0.6 mmol) in toluene (1.0 ml), 1-octanol (130 mg, 1 mmol) and vinyl acetate (2 mmol) were added, followed by stirring at 100° C. in an atmosphere of argon gas for 2 hours. The reaction mixture was analyzed by gas chromatography to find that 1-octyl vinyl ether and octyl acetate were produced in yields of 90% and 1%, respectively, with a conversion from 1-octanol of 98%.

Example 41

To a mixture of di-μ-chlorobis(1,5-cyclooctadiene)diiridium(I) [Ir(cod)Cl]$_2$ (0.01 mmol) and sodium carbonate (0.6 mmol) in toluene (1.0 ml), 2-cyclopenten-1-ol (1 mmol) and vinyl acetate (2 mmol) were added, followed by stirring at 100° C. in an atmosphere of argon gas for 2 hours. The reaction mixture was analyzed by gas chromatography to find that 2-cyclopenten-1-yl vinyl ether and 2-cyclopenten-1-one were produced in yields of 34% and 14%, respectively, with a conversion from 2-cyclopenten-1-ol of 69%.

Example 42

To a mixture of di-μ-chlorobis(1,5-cyclooctadiene)diiridium(I) [Ir(cod)Cl]$_2$ (0.01 mmol) and sodium acetate (1.2 mmol) in toluene (2.0 ml), triethylene glycol (1 mmol) and vinyl acetate (4 mmol) were added, followed by stirring at 100° C. in an atmosphere of argon gas for 6 hours. The reaction mixture was analyzed by gas chromatography to find that triethylene glycol divinyl ether, triethylene glycol monovinyl ether, and triethylene glycol monovinyl ether monoacetate were produced in yields of 63%, 3%, and 18%, respectively, with a conversion from triethylene glycol of 100%.

Other embodiments and variations will be obvious to those skilled in the art, and this invention is not to be limited to the specific matters stated above.

What is claimed is:

1. A process for producing vinyl ether compounds, comprising the step of:

reacting a vinyl ester compound represented by following Formula (1):

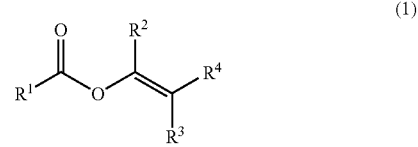

(1)

wherein $R^1$, $R^2$, $R^3$ and $R^4$ are the same or different and are each a hydrogen atom or an organic group selected from the group consisting of a halogen atom, an alkyl group, a haloalkyl group, an aryl group, a hydroxyl group optionally protected by a protecting group, a hydroxymethyl group optionally protected by a protecting group, an amino group optionally protected by a protecting group, a carboxyl group optionally protected by a protecting group, a sulfo group optionally protected by a protecting group, an oxo group, a nitro group, a cyano group, an acyl group optionally protected by a protecting group, a hydrocarbon group optionally having a substituent and a heterocyclic group optionally having a substituent, wherein said organic group does not adversely affect the reaction, with a hydroxy compound represented by following Formula (2):

 R⁵OH (2)

wherein R⁵ is an organic group having the same meaning as defined above for R¹–R⁴, in the presence of at least one transition element selected from the group consisting of iron, cobalt, nickel, ruthenium, rhodium, osmium, iridium and platinum, to thereby yield a vinyl ether compound represented by following Formula (3):

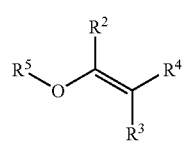
(3)

wherein R², R³, R⁴ and R⁵ have the same meanings as defined above.

2. The process according to claim 1 wherein the transition element compound is an iridium compound.

3. The process according to claim 1 wherein the vinyl ester compound represented by Formula (1) is allowed to react with the hydroxy compound represented by Formula (2) in the presence of a base.

4. The process of claim 1, wherein said organic group is the hydrocarbon group optionally having a substituent or the heterocyclic group optionally having a substituent.

5. The process of claim 1, wherein said vinyl ester (1) is reacted with said hydroxy compound (2) at a temperature ranging from 50° C. to 200° C.

6. The process of claim 1, wherein said vinyl ester (1) is reacted with said hydroxy compound (2) at a temperature ranging from 50° C. to 150° C.

* * * * *